United States Patent
Ishii et al.

(10) Patent No.: US 10,274,612 B2
(45) Date of Patent: Apr. 30, 2019

(54) RADIATION IMAGING APPARATUS AND PHOTON COUNTING METHOD

(71) Applicant: CANON KABUSHIKI KAISHA, Tokyo (JP)

(72) Inventors: Yoshiaki Ishii, Kawasaki (JP); Atsushi Iwashita, Tokyo (JP); Sho Sato, Tokyo (JP); Kosuke Terui, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/751,600

(22) PCT Filed: Oct. 13, 2016

(86) PCT No.: PCT/JP2016/004569
§ 371 (c)(1),
(2) Date: Feb. 9, 2018

(87) PCT Pub. No.: WO2017/081837
PCT Pub. Date: May 18, 2017

(65) Prior Publication Data
US 2018/0239033 A1   Aug. 23, 2018

(30) Foreign Application Priority Data

Nov. 13, 2015   (JP) ................................ 2015-223341

(51) Int. Cl.
*H01L 27/146* (2006.01)
*G01T 1/20* (2006.01)
(Continued)

(52) U.S. Cl.
CPC ............. *G01T 1/20* (2013.01); *A61B 6/4233* (2013.01); *A61B 6/4241* (2013.01); *G01T 1/17* (2013.01);
(Continued)

(58) Field of Classification Search
CPC .. H04N 5/3741; H04N 5/37452; H04N 5/361; H04N 5/32; G06K 9/00013;
(Continued)

(56) References Cited

U.S. PATENT DOCUMENTS 6,212,234 B1 * 4/2001 Andoh .................... G06T 9/004
375/240.08
8,829,438 B2   9/2014 Sato et al.
(Continued)

FOREIGN PATENT DOCUMENTS

| JP | 2003-279411 | 10/2003 |
|----|-------------|---------|
| JP | 2009-273630 | 11/2009 |

OTHER PUBLICATIONS

U.S. Appl. No. 15/563,148, Kosuke Terui, filed Sep. 29, 2017.
(Continued)

*Primary Examiner* — Kiho Kim
(74) *Attorney, Agent, or Firm* — Venable LLP

(57) ABSTRACT

A radiation imaging apparatus comprising a pixel array in which a plurality of pixels are arrayed and a processor configured to generate a radiation image based on radio-photons which have entered the pixel array, wherein the processor performs a first process of obtaining a value of a signal from each of the plurality of pixels as a pixel value, a second process of selecting at least one of the plurality of pixels as a reference pixel, and a third process of specifying a detection area of a radio-photon in the pixel array by sequentially referring to pixel values of pixels around the reference pixel as a starting point.

18 Claims, 12 Drawing Sheets

(51) Int. Cl.
  *G01T 1/17* (2006.01)
  *H04N 5/32* (2006.01)
  *G01T 1/24* (2006.01)
  *H04N 5/361* (2011.01)
  *A61B 6/00* (2006.01)

(52) U.S. Cl.
  CPC ............... *G01T 1/247* (2013.01); *H04N 5/32* (2013.01); *H04N 5/361* (2013.01); *A61B 6/482* (2013.01); *A61B 6/542* (2013.01)

(58) Field of Classification Search
  CPC ......... G06K 9/00067; G01T 1/20; G01T 1/00; G01T 1/247; G01T 1/17; A61B 6/4241; A61B 6/4233; A61B 6/542; A61B 6/482
  See application file for complete search history.

(56) References Cited

U.S. PATENT DOCUMENTS

| | | | |
|---|---|---|---|
| 8,854,521 B2 * | 10/2014 | Yamashita | H04N 5/376 348/294 |
| 9,048,154 B2 | 6/2015 | Takenaka et al. | |
| 9,128,196 B2 | 9/2015 | Sato et al. | |
| 9,134,432 B2 | 9/2015 | Iwashita et al. | |
| 9,185,319 B2 * | 11/2015 | Mayer | H01L 27/14603 |
| 9,234,966 B2 | 1/2016 | Sugawara et al. | |
| 9,363,456 B2 * | 6/2016 | Krymski | H01L 27/14607 |
| 9,423,512 B2 | 8/2016 | Sato et al. | |
| 9,445,030 B2 | 9/2016 | Yagi et al. | |
| 9,462,989 B2 | 10/2016 | Takenaka et al. | |
| 9,468,414 B2 | 10/2016 | Ryu et al. | |
| 9,470,800 B2 | 10/2016 | Iwashita et al. | |
| 9,470,802 B2 | 10/2016 | Okada et al. | |
| 9,541,653 B2 | 1/2017 | Iwashita et al. | |
| 9,655,586 B2 | 5/2017 | Yagi et al. | |
| 9,737,271 B2 | 8/2017 | Iwashita et al. | |
| 9,812,474 B2 | 11/2017 | Yagi et al. | |
| 10,037,468 B2 * | 7/2018 | Yaguchi | G06K 9/00765 |
| 2003/0228037 A1 * | 12/2003 | Endo | G06K 9/00013 382/124 |
| 2011/0043675 A1 * | 2/2011 | Matsuda | H04N 5/3741 348/300 |
| 2011/0317054 A1 | 12/2011 | Kameshima et al. | |
| 2014/0112448 A1 | 4/2014 | Takenaka et al. | |
| 2014/0239186 A1 | 8/2014 | Sato et al. | |
| 2014/0284491 A1 | 9/2014 | Sato et al. | |
| 2014/0361189 A1 | 12/2014 | Kameshima et al. | |
| 2015/0077590 A1 * | 3/2015 | Kuriyama | H04N 5/3745 348/231.99 |
| 2015/0358571 A1 * | 12/2015 | Dominguez Castro | H04N 5/345 348/308 |
| 2016/0050378 A1 * | 2/2016 | Wu | H04N 5/3696 348/77 |
| 2016/0084969 A1 | 3/2016 | Sato et al. | |
| 2016/0178764 A1 | 6/2016 | Ryu et al. | |
| 2016/0270755 A1 | 9/2016 | Takenaka et al. | |

OTHER PUBLICATIONS

U.S. Appl. No. 15/564,946, Kosuke Terui, filed Oct. 6, 2017.
U.S. Appl. No. 15/791,566, Atsushi Iwashita, filed Oct. 24, 2017.

* cited by examiner

[Fig. 1]
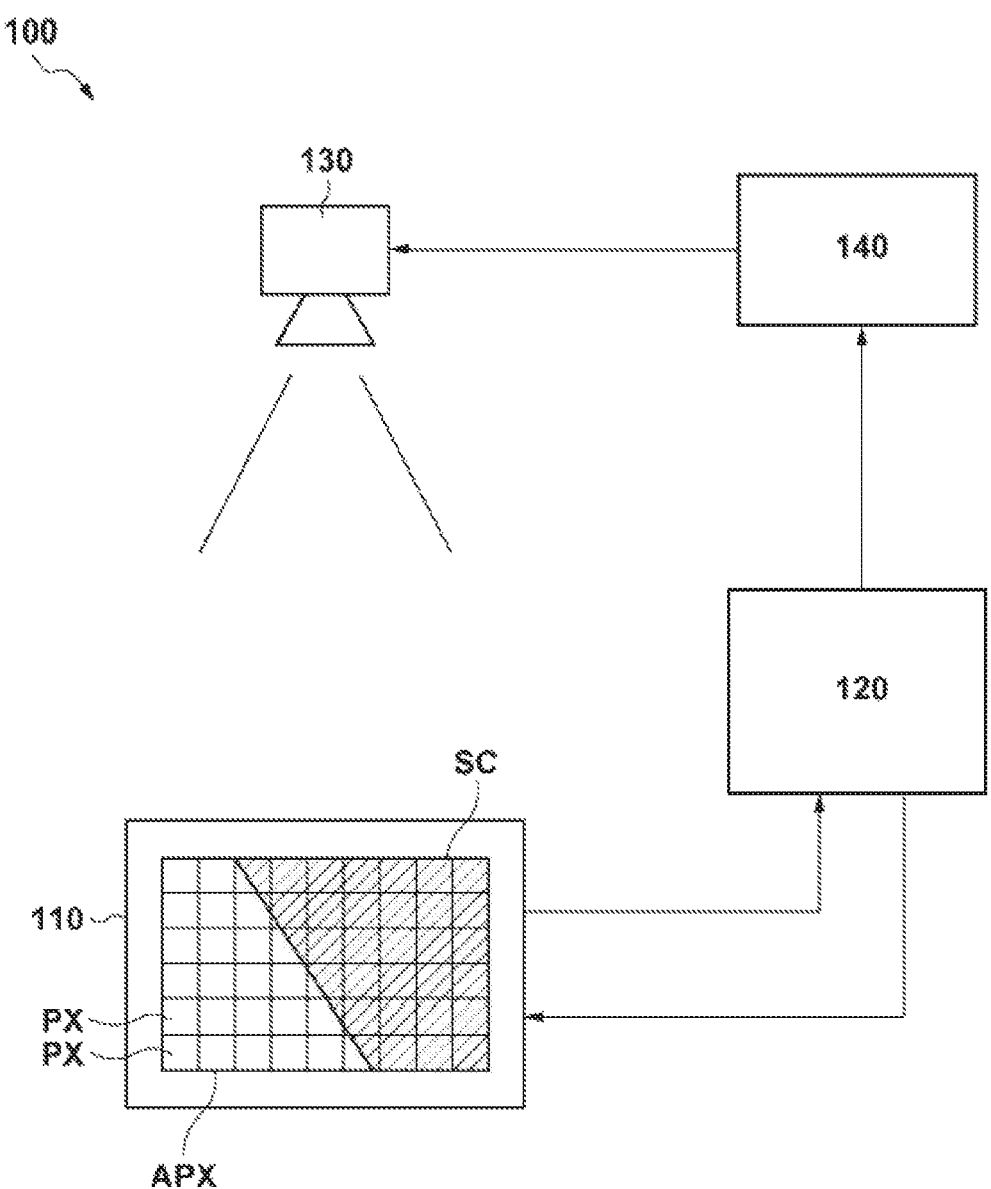

[Fig. 2]
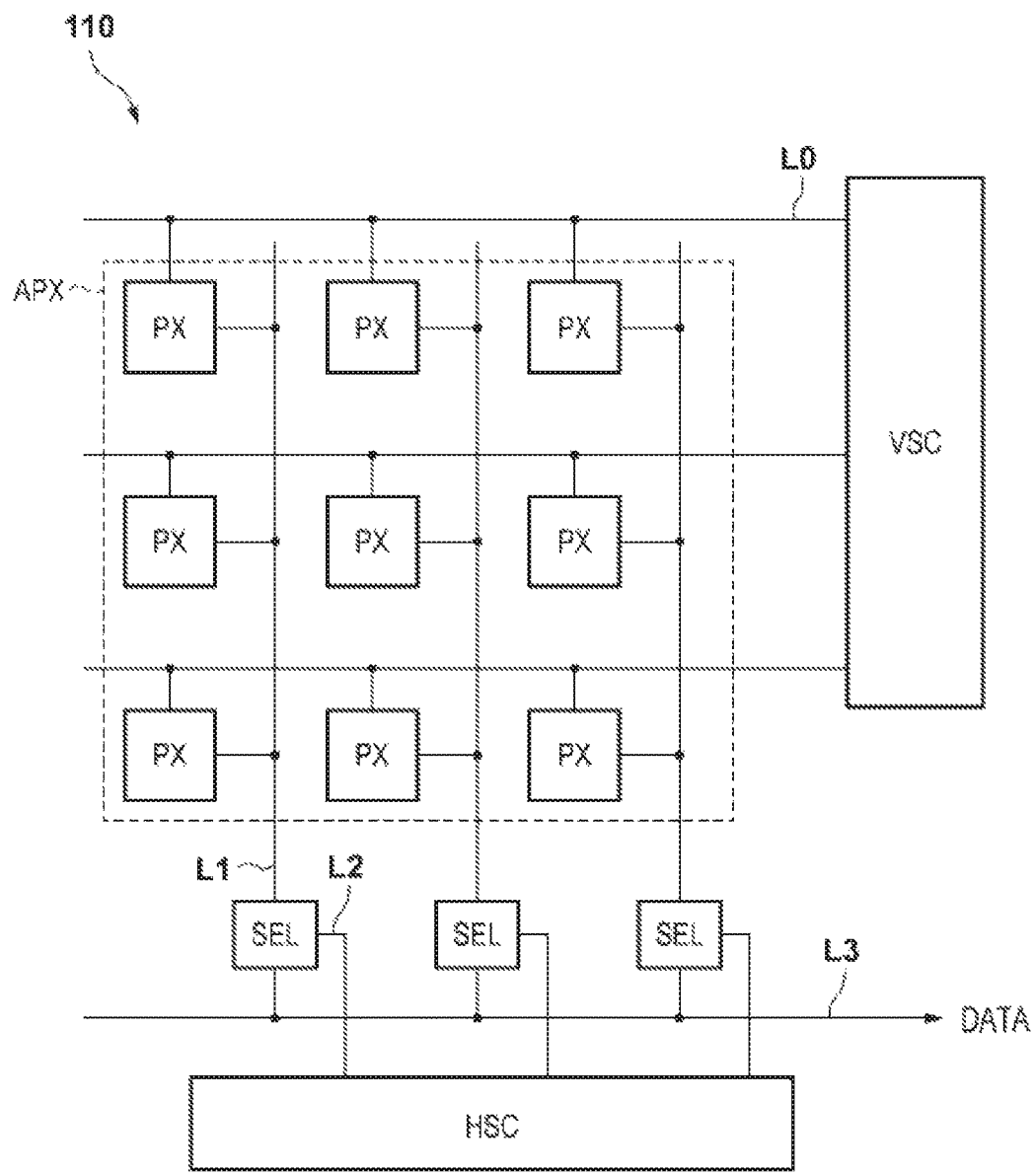

[Fig. 3]
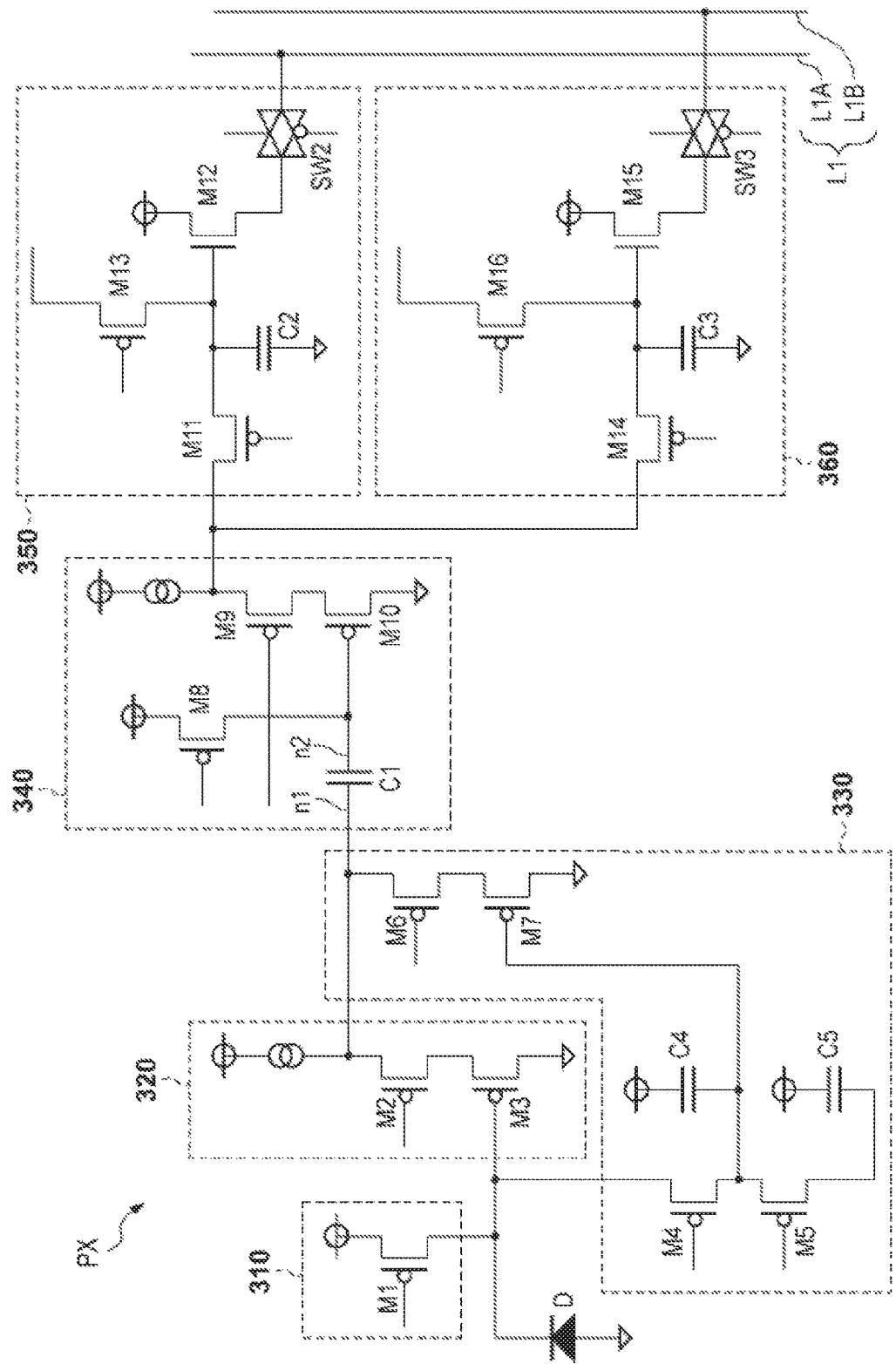

[Fig. 4]
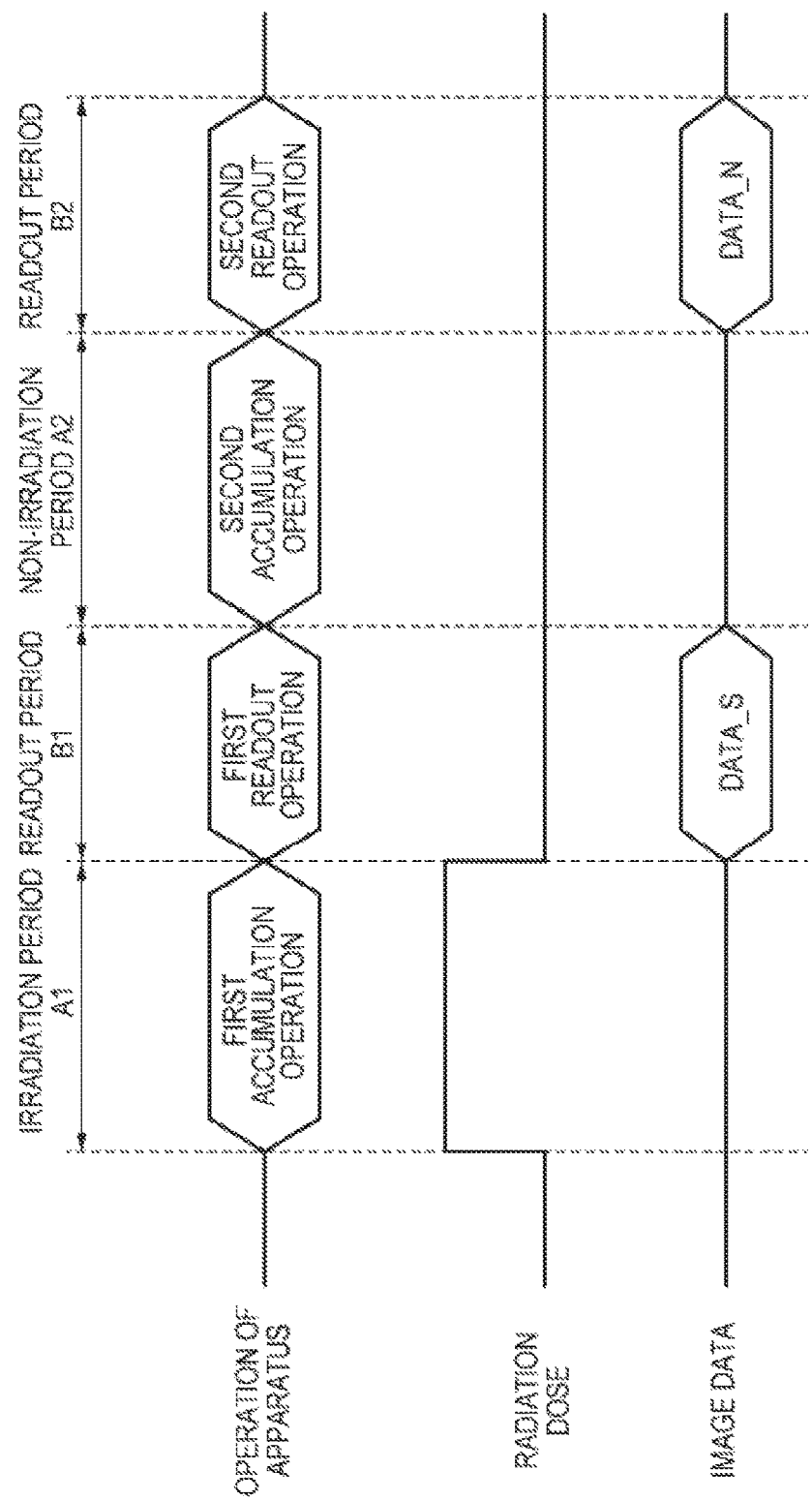

[Fig. 5A]
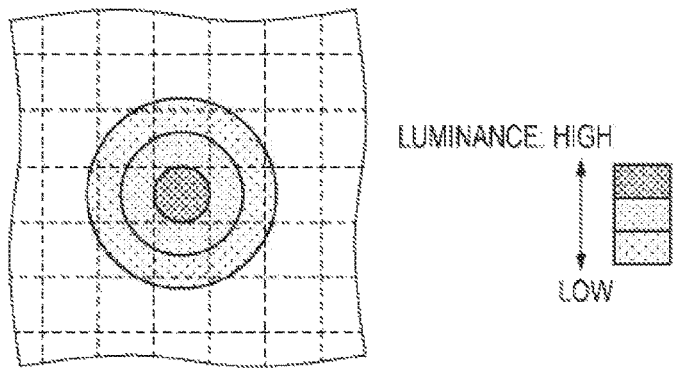
[Fig. 5B]
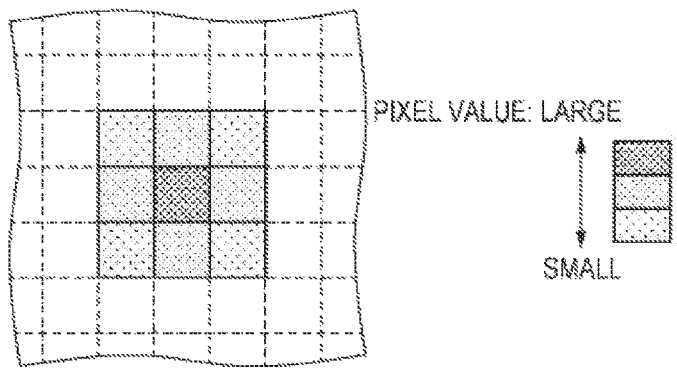
[Fig. 5C]
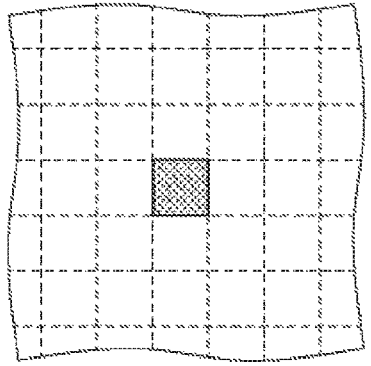

[Fig. 6]
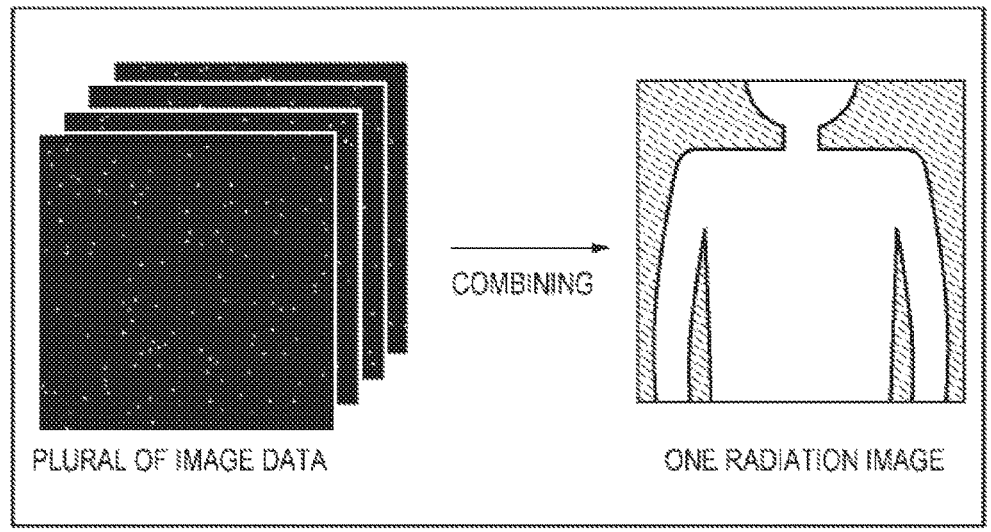
[Fig. 7A]
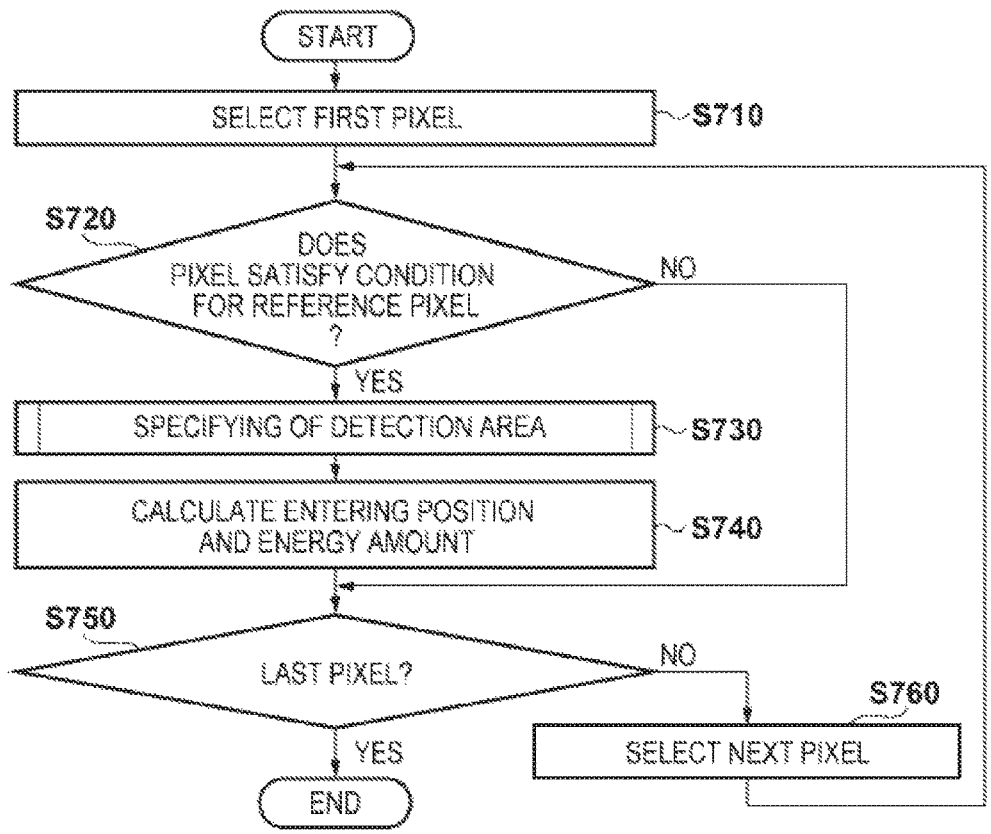

[Fig. 7B]
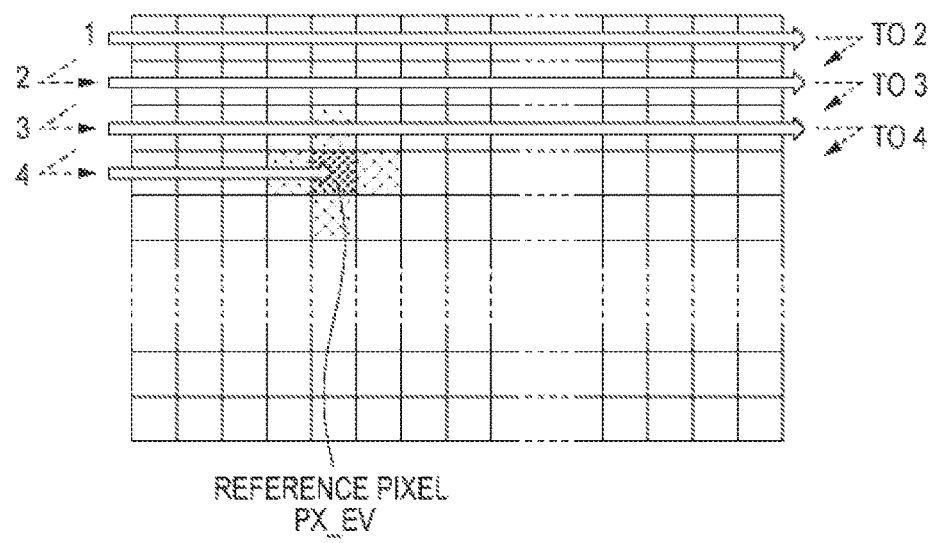
[Fig. 7C]

[Fig. 8]
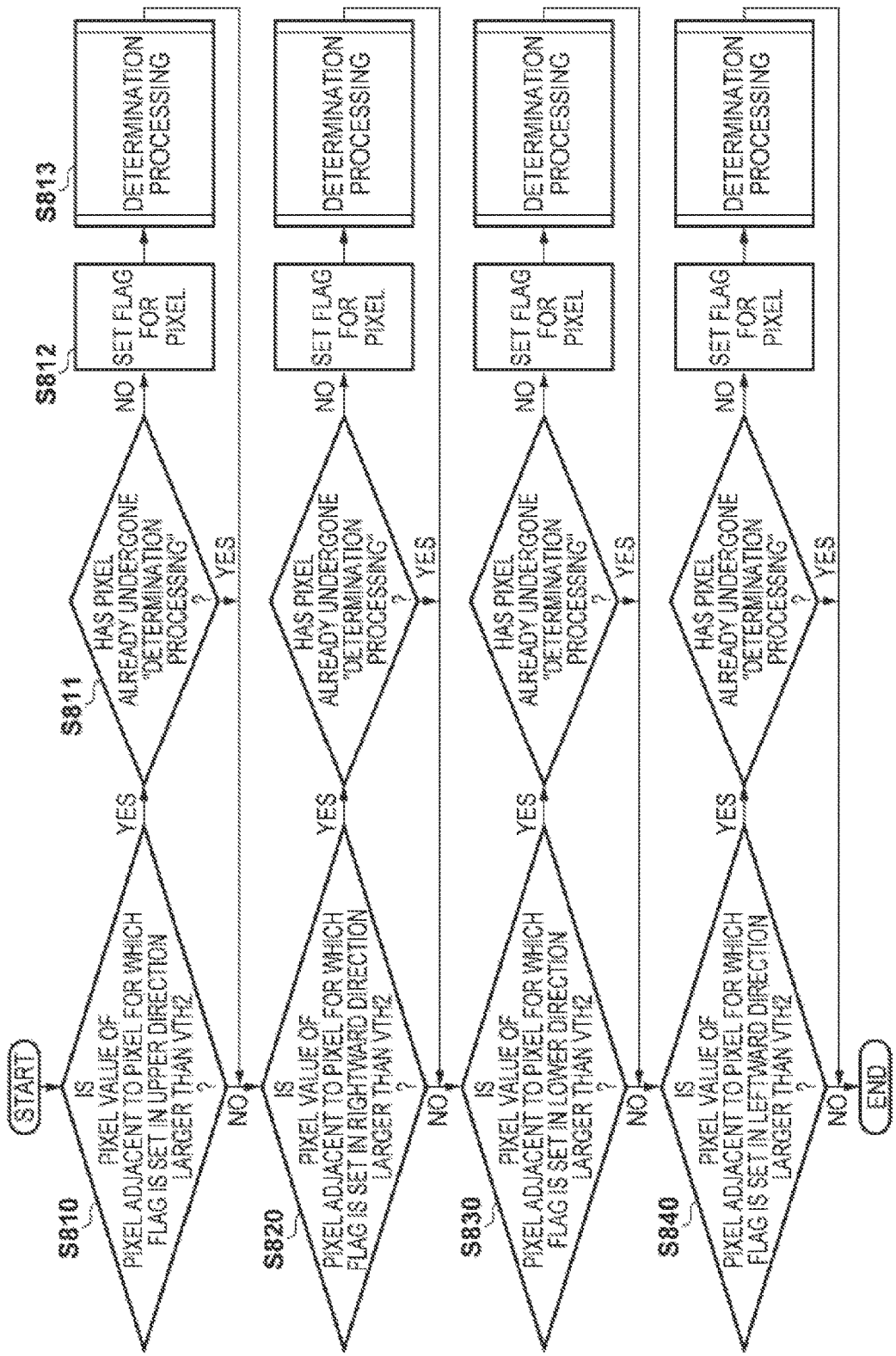

[Fig. 9A]

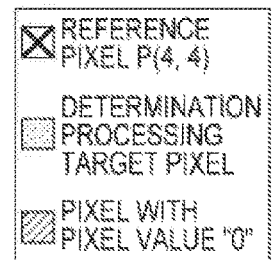

"DETERMINATION PROCESSING" IS PERFORMED WITH RESPECT TO REFERENCE PIXEL PX(4, 4). MORE SPECIFICALLY, IT IS DETERMINED WHETHER PIXEL VALUE OF EACH OF FOUR ADJACENT PIXELS ADJACENT TO REFERENCE PIXEL IS LARGER THAN VTH2.

⊠ REFERENCE PIXEL P(4, 4)
☐ DETERMINATION PROCESSING TARGET PIXEL
▨ PIXEL WITH PIXEL VALUE "0"

[Fig. 9B]

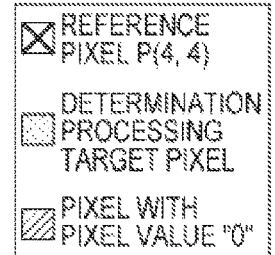

"DETERMINATION PROCESSING" IS PERFORMED WITH RESPECT TO EACH PIXEL DETERMINED IN STEP IN FIG. 9A TO BE LARGER IN PIXEL VALUE THAN VTH2. IN THIS CASE, FIRST OF ALL, "DETERMINATION PROCESSING" IS PERFORMED WITH RESPECT TO PIXEL PX(3, 4).

⊠ REFERENCE PIXEL P(4, 4)
☐ DETERMINATION PROCESSING TARGET PIXEL
▨ PIXEL WITH PIXEL VALUE "0"

[Fig. 9C]

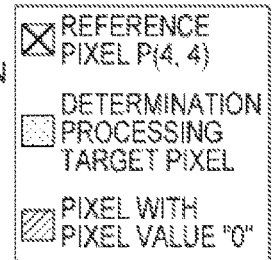

"DETERMINATION PROCESSING" IS PERFORMED WITH RESPECT TO EACH PIXEL DETERMINED IN STEP IN FIG. 9B TO BE LARGER IN PIXEL VALUE THAN VTH2 (NOTE HOWEVER THAT "DETERMINATION PROCESSING" IS OMITTED WITH RESPECT TO PIXEL WHICH HAS ALREADY UNDERGONE DETERMINATION PROCESSING).

⊠ REFERENCE PIXEL P(4, 4)
☐ DETERMINATION PROCESSING TARGET PIXEL
▨ PIXEL WITH PIXEL VALUE "0"

[Fig. 9D]

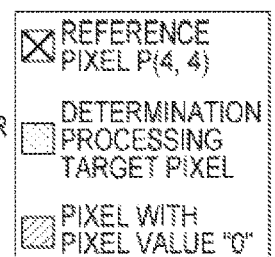

"DETERMINATION PROCESSING" IS PERFORMED WITH RESPECT TO EACH PIXEL DETERMINED IN STEP IN FIG. 9C TO BE LARGER IN PIXEL VALUE THAN VTH2 (NOTE HOWEVER THAT "DETERMINATION PROCESSING" IS OMITTED WITH RESPECT TO PIXEL HAVING ALREADY UNDERGONE DETERMINATION PROCESSING).

⊠ REFERENCE PIXEL P(4, 4)
☐ DETERMINATION PROCESSING TARGET PIXEL
▨ PIXEL WITH PIXEL VALUE "0"

[Fig. 9E]

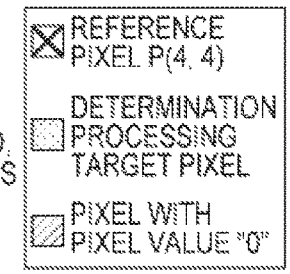

SINCE NO PIXEL DETERMINED IN STEP IN FIG. 9D TO BE LARGER IN PIXEL VALUE THAN VTH2 OR "DETERMINATION PROCESSING" HAS ALREADY BEEN PERFORMED, "DETERMINATION PROCESSING" IS PERFORMED WITH RESPECT TO ANOTHER PIXEL PX(4, 5) DETERMINED IN STEP IN FIG. 9A TO BE LARGER IN PIXEL VALUE THAN VTH2.

[Fig. 9F]

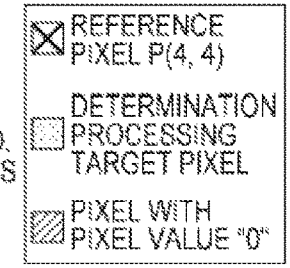

SINCE NO PIXEL DETERMINED IN STEP IN FIG. 9E TO BE LARGER IN PIXEL VALUE THAN VTH2 OR "DETERMINATION PROCESSING" HAS ALREADY BEEN PERFORMED, "DETERMINATION PROCESSING" IS PERFORMED WITH RESPECT TO ANOTHER PIXEL PX(4, 4) DETERMINED IN STEP IN FIG. 9A TO BE LARGER IN PIXEL VALUE THAN VTH2.

[Fig. 9G]

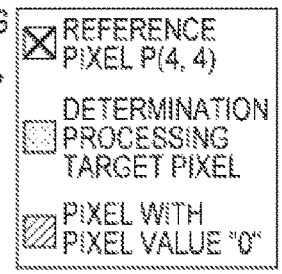

"DETERMINATION PROCESSING" IS PERFORMED WITH RESPECT TO EACH PIXEL DETERMINED IN STEP IN FIG. 9F TO BE LARGER IN PIXEL VALUE THAN VTH2.

[Fig. 9H]

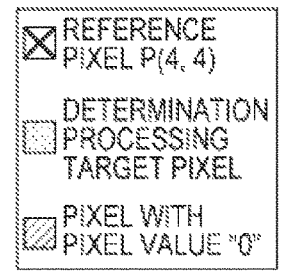

SIMILAR PROCEDURE IS REPEATED TO SPECIFY DETECTION AREA OF RADIO-PHOTON.

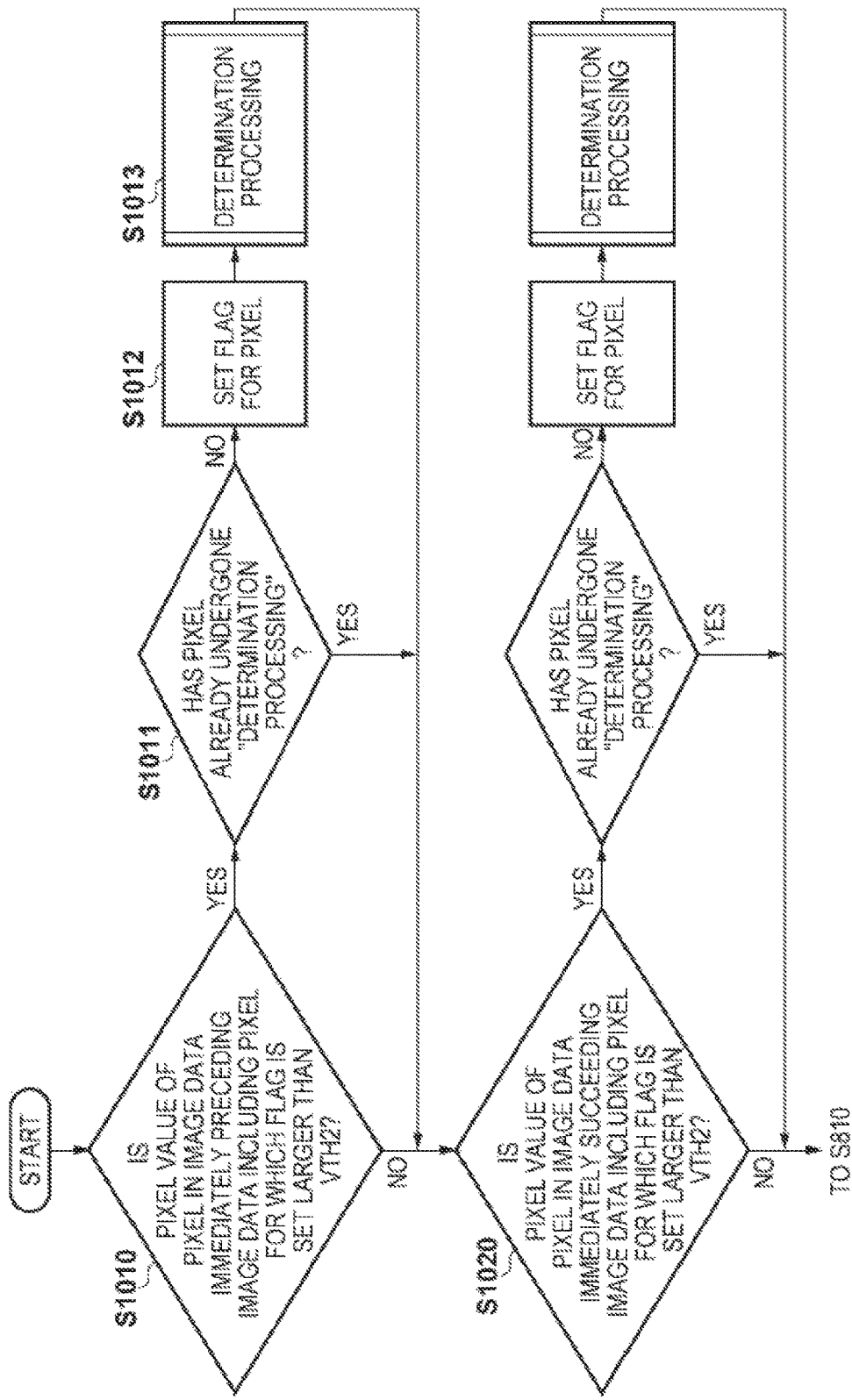
[Fig. 10]

[Fig. 11]
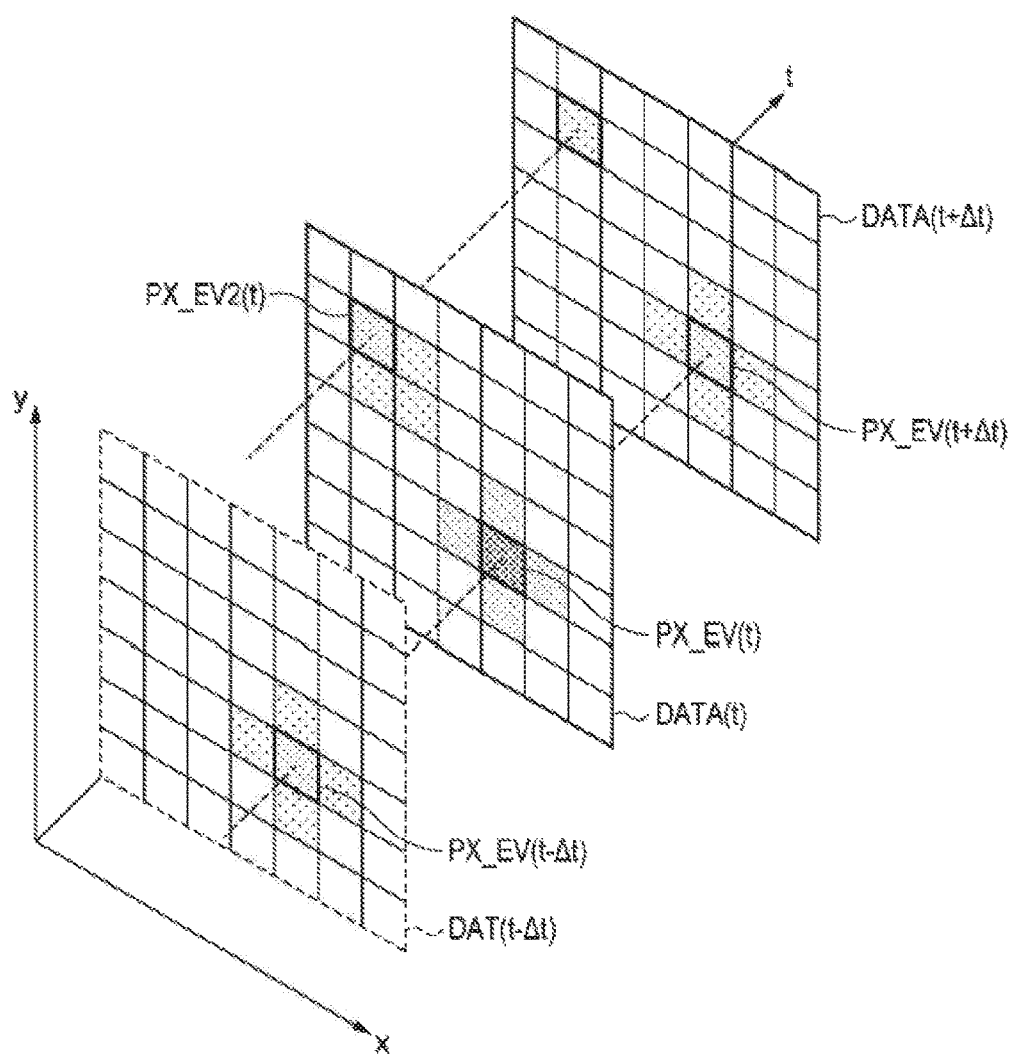

RADIATION IMAGING APPARATUS AND PHOTON COUNTING METHOD

This application is a national phase of PCT/JP2016/004569 filed Oct. 13, 2016, which in turn claims the benefit of Japanese Patent Application No. 2015-223341 filed Nov. 13, 2015, which are hereby incorporated by reference herein in their entirety.

TECHNICAL FIELD

The present invention relates to a radiation imaging apparatus and a photon counting method.

BACKGROUND ART

Some radiation imaging apparatus performs radiation imaging by a photon counting scheme of detecting each radio-photon and counting the number of photons. More specifically, the radiation imaging apparatus includes, for example, a pixel array having an array of a plurality of pixels and a processor. When a radio-photon enters the pixel array, each of pixels corresponding to the entering position of the radio-photon and positions near it in the pixel array outputs a signal corresponding to the amount of energy of the radio-photon.

The processor obtains a plurality of pixel data by reading out signals from a plurality of pixels as one (one-frame) pixel data in a predetermined cycle, and generates radiation image data by using the plurality of pixel data. More specifically, the processor calculates the entering position of a radio-photon and its energy amount based on a signal forming each of a plurality of pixel data, and generates radiation image data based on the calculation result.

As one of the above calculation methods, there may be available a method of specifying the detection areas of radio-photons in a pixel array based on image data and calculating the entering positions and energy amounts of the radio-photons based on the respective pixel signals in the detection areas.

SUMMARY OF INVENTION

The present invention therefore provides a novel technique for specifying the detection areas of radio-photons in a pixel array.

One of the aspects of the present invention provides a radiation imaging apparatus comprising a pixel array in which a plurality of pixels are arrayed and a processor configured to generate a radiation image based on radio-photons which have entered the pixel array, wherein the processor performs a first process of obtaining a value of a signal from each of the plurality of pixels as a pixel value, a second process of selecting at least one of the plurality of pixels as a reference pixel, and a third process of specifying a detection area of a radio-photon in the pixel array by sequentially referring to pixel values of pixels around the reference pixel as a starting point.

Further features of the present invention will become apparent from the following description of exemplary embodiments with reference to the attached drawings.

BRIEF DESCRIPTION OF DRAWINGS

FIG. 1 is a view showing an example of the arrangement of a radiation imaging apparatus;

FIG. 2 is a block diagram showing an example of the arrangement of an imaging unit;

FIG. 3 is a circuit diagram showing an example of the arrangement of a pixel;

FIG. 4 is an example of an operation timing chart of the radiation imaging apparatus;

FIG. 5A is a view for explaining the relationship between the emission distribution of a scintillator and image data;

FIG. 5B is a view for explaining the relationship between the emission distribution of a scintillator and image data;

FIG. 5C is a view for explaining the relationship between the emission distribution of a scintillator and image data;

FIG. 6 is a view for explaining an example of a processing result on a plurality of image data;

FIG. 7A is a view for explaining an example of a radio-photon detection method;

FIG. 7B is a view for explaining an example of a radio-photon detection method;

FIG. 7C is a view for explaining an example of a radio-photon detection method;

FIG. 8 is a flowchart for explaining an example of a method of specifying the detection areas of radio-photons in a pixel array;

FIG. 9A is a view for explaining an example of a detection area specifying method;

FIG. 9B is a view for explaining an example of a detection area specifying method;

FIG. 9C is a view for explaining an example of a detection area specifying method;

FIG. 9D is a view for explaining an example of a detection area specifying method;

FIG. 9E is a view for explaining an example of a detection area specifying method;

FIG. 9F is a view for explaining an example of a detection area specifying method;

FIG. 9G is a view for explaining an example of a detection area specifying method;

FIG. 9H is a view for explaining an example of a detection area specifying method;

FIG. 10 is a flowchart for explaining an example of a detection area specifying method; and FIG. 11 is a view for explaining an example of a detection area specifying method.

DESCRIPTION OF EMBODIMENTS

The preferred embodiments of the present invention will be described below with reference to the accompanying drawings. The same reference numerals in the respective drawings denote the same members or the same constituent elements, and a repetitive description will be omitted in each of the following embodiments.

First Embodiment

FIG. 1 is a view showing an example of the arrangement of a radiation imaging apparatus 100 (or may be referred to as a "radiation imaging system"). The radiation imaging apparatus 100 includes an imaging unit 110 which images an object irradiated with radiation, a processor 120 which processes a signal from the imaging unit 110, a radiation source 130 which generates radiation, and a radiation control unit 140 which controls the radiation source 130. Assume that the concept of radiation includes, for example, α-rays and β-rays in addition to X-rays generally used for radiation imaging.

The imaging unit 110 includes a scintillator SC which converts radiation into light and a pixel array APX having a plurality of pixels PX arrayed in a matrix pattern. More specifically, in the pixel array APX, the plurality of pixels PX which detect light (scintillation light) from the scintillator SC are arrayed to form a plurality of rows and a plurality of columns. Each pixel PX may also be called a "sensor", and the pixel array APX may also be called a "sensor array".

The processor 120 performs, for example, radiation imaging by controlling the imaging unit 110 and the radiation control unit 140. More specifically, the processor 120 performs radiation imaging by a photon counting scheme of receiving image data or a pixel signal which forms the image data from the imaging unit 110 and counting the number of radio-photons detected by the pixel array APX. The processor 120 generates data for displaying a radiation image on a display unit (not shown) such as a display based on a radio-photon counting result. The processor 120 may perform predetermined correction processing for the data.

Although the processor 120 may also function as a driving unit which drives the respective units described above and the respective elements constituting them while synchronously controlling them, the driving unit may be arranged separately from the processor 120. The processor 120 may be a personal computer storing programs or software for implementing operations described in this specification or an arithmetic device including a dedicated integrated circuit (for example, ASIC).

The arrangement of the radiation imaging apparatus 100 is not limited to the above example, and may be configured such that some functions of a given unit may be incorporated in another unit or some units may be integrated into one unit. For example, although the radiation control unit 140 and the processor 120 are individually arranged in the above case, they may be implemented by a single unit.

FIG. 2 shows an example of the arrangement of the imaging unit 110. The imaging unit 110 includes, for example, the pixel array APX having an array of the plurality of pixels PX, a vertical scanning circuit VSC, a horizontal scanning circuit HSC, and a selection circuit SEL. In this case, for the sake of easy understanding, FIG. 2 exemplarily shows an arrangement having the pixels PX arrayed in 3 rows×3 columns. In practice, however, a larger number of pixels can be arrayed. For example, in the case of a 17-inch sensor panel, the pixels PX can be arrayed in about 2,800 rows×about 2,800 columns.

The vertical scanning circuit VSC functions as a pixel driving unit for driving the plurality of pixels PX and can be formed from a shift register or the like. More specifically, the vertical scanning circuit VSC controls the plurality of pixels PX for each row by using a signal line L0 corresponding to each row. Although the following will exemplify a form having one signal line L0 for each row, two or more signal lines may be arranged for each row. Signals from the pixels PX are output to the selection circuit SEL via a corresponding column signal line L1.

The horizontal scanning circuit HSC and the selection circuit SEL function as a reading unit for reading out a signal from each pixel PX. More specifically, the horizontal scanning circuit HSC is constituted by, for example, a shift register and the like. The horizontal scanning circuit HSC controls the selection circuit SEL by using a signal line L2 corresponding to each column, and reads out signals from the pixels PX on a corresponding column and are driven by the vertical scanning circuit VSC. The readout signals are horizontally transferred via an output line L3 and output as pixel signals which form part of image data DATA or obtain the image data DATA.

FIG. 3 shows an example of the arrangement of the unit pixel PX. Each pixel PX includes, for example, a detection element D, a reset unit 310, a signal amplifying unit 320, a photosensitivity selection unit 330, a clamp unit 340, a first sampling unit 350, and a second sampling unit 360.

The detection element D includes, for example, a photoelectric conversion element such as a PIN sensor or MIS sensor. The reset unit 310 includes a transistor M1. The potential of the detection element D is reset by setting the transistor M1 in a conductive state. The signal amplifying unit 320 includes transistors M2 and M3 connected to a current source. When the transistor M2 is set in a conductive state, the transistor M3 performs a source follower operation. This will amplify a signal corresponding to the amount of charge generated by the detection element D.

The photosensitivity selection unit 330 includes transistors M4 to M7 and capacitors C4 and C5. For example, setting the transistor M4 in a conductive state connects the capacitor C4 to the gate of the transistor M3. In addition, setting the transistor M6 in a conductive state causes the transistor M7 to perform a source follower operation. This makes it possible to change the gain of a signal in accordance with the amount of charge generated by the detection element D. Furthermore, setting the transistor M5 in a conductive state can further change the signal gain by connecting the capacitor C4 to the gate of the transistor M3.

The clamp unit 340 includes transistors M8 to M10 and a capacitor C1. An output from the signal amplifying unit 320 when the detection element D is reset is supplied to one terminal n1 of the capacitor C1, and a power supply voltage is supplied to the other terminal n2 of the capacitor C1 when the transistor M8 is set in a conductive state. This will clamp a voltage when the detection element D is reset, as a noise component, between the terminals n1 and n2. Subsequently, when the transistor M8 is set in a non-conductive state and the transistor M9 is set in a conductive state, the transistor M10 performs a source follow operation. The source follower operation of the transistor M10 amplifies a signal corresponding to a change in the voltage of the terminal n2 accompanying the detection of scintillation light by the detection element D. The amplified signal is then output to the sampling unit 350 or 360.

The sampling unit 350 includes transistors M11 to M13, a capacitor C2, and an analog switch SW2, and samples a signal (S signal) equivalent to the amount of scintillation light detected by the detection element D. More specifically, it is possible to sample a signal from the clamp unit 340 and hold it in the capacitor C2 by controlling the transistor M11. The transistor M12 which performs a source follower operation amplifies the signal, and outputs it to a column signal line L1A (one of the column signal lines L1) via the analog switch SW2.

Note that the transistor M13 can be arranged on an electric path between the capacitor C2 and a capacitor C2 of another neighboring pixel (for example, a pixel PX'). Setting the transistor M13 in a conductive state can obtain the average of the S signals from the pixels PX and PX'. It is also possible to reduce the difference in noise component between these signals.

The second sampling unit 360 has the same arrangement as that of the first sampling unit 350, and samples a signal (N signal) equivalent to a noise component. A transistor M15 which performs a source follower operation amplifies the sampled N signal and outputs the signal to a column signal line L1B (the other one of the column signal lines L1) via an analog switch SW3.

FIG. 4 schematically exemplifies a driving timing chart for the radiation imaging apparatus 100. Referring to FIG. 4, the abscissa represents a time axis, and the ordinate represents the operations of the apparatus 100, radiation doses (a high level representing an irradiation state, and a low level representing a non-irradiation state), and image data (or a group of pixel signals forming image data) output via the output line L3.

For example, first of all, the radiation source 130 irradiates the pixel array APX with radiation over a predetermined period. Referring to FIG. 4, this period is referred to as an "irradiation period A1". In the period A1, each pixel PX of the pixel array APX generates and accumulates the amount of charge corresponding to the irradiation dose of radiation (FIG. 4 shows this operation as the "first accumulation operation"). Subsequently, in a readout period B1, the S signal is read out from each of the plurality of pixels PX of the pixel array APX (FIG. 4 shows this operation as the "first readout operation"). The readout S signal corresponds to the amount of charge accumulated in the pixel PX in the period A1. Referring to FIG. 4, image data formed from the readout S signal will be referred to as "image data DATA_S".

Subsequently, the radiation imaging apparatus 100 stands by over a period almost equal to the period A1 while the pixel array APX is not irradiated with radiation. FIG. 4 shows this period as a "non-irradiation period A2". In the period A2, each pixel PX of the pixel array APX generates and accumulates the amount of charge corresponding to a noise component (FIG. 4 shows this operation as a "second accumulation operation"). Subsequently, in a readout period B2, the N signal is read out from each pixel PX of the pixel array APX (FIG. 4 shows this operation as a "second readout operation"). The readout N signal corresponds to the amount of charge accumulated in the pixel PX in the period A2. Referring to FIG. 4, image data formed from the readout N signal will be referred to as "image data DATA_N" hereinafter (the image data DATA_N can also be referred to as dark image data or offset image data).

The processor 120 calculates the difference between the image data DATA_S and the image data DATA_N to obtain one (one-frame) image data DATA. Although described in detail later, the processor 120 obtains a plurality of image data DATA by performing the above series of operations in a predetermined cycle.

FIG. 5A shows the emission distribution of the scintillator SC in correspondence with positions on the pixel array APX. In this case, as a radio-photon enters the scintillator SC, scintillation light is generated. Most of scintillation light propagates to the pixel PX corresponding to the entering position of the radio-photon and is detected by the pixel PX. Along with this operation, part of the scintillation light can be diffused in the horizontal direction (a direction parallel to the upper surface of the pixel array APX). For this reason, as shown in FIG. 5A, part of the scintillation light can be detected by the other pixels PX around (near) the above corresponding pixel PX.

FIG. 5B shows image data in the case of the emission distribution in FIG. 5A. Referring to FIG. 5B, each of squares delimited by the broken lines in a matrix pattern corresponds to a pixel position on the pixel array APX. In addition, each square includes the value of a pixel signal of the pixel PX at the corresponding pixel position or the value obtained by quantizing the pixel signal (to be referred to as the "pixel value" hereinafter). FIG. 5B shows, for example, that as scintillation light is diffused in the horizontal direction, other neighboring pixels PX can have pixel values larger than 0 even though they are smaller than the pixel value of the corresponding pixel PX.

FIG. 5C shows image data to be calculated based on the image data in FIG. 5B, which is image data obtained by calculating the entering position and energy amount of a radio-photon in the pixel array APX. That is, the entering position and energy amount of a radio-photon can be calculated based on the pixel value of the above corresponding pixel PX and the pixel values of other neighboring pixels PX. More specifically, the entering position of a radio-photon corresponds to the position of a pixel having the largest pixel position in FIG. 5B, and the energy amount of the radio-photon can correspond to a value obtained by adding the pixel value of the corresponding pixel and the pixel value of each neighboring pixel.

FIG. 6 is a view for explaining an example of a processing result on a plurality of image data. As described above, the processor 120 obtains a plurality of image data DATA by performing the series of operations described above with reference to FIG. 4 in a predetermined cycle. The processor 120 calculates the entering positions and energy amounts of radio-photons with respect to the plurality of image data DATA. The processor 120 generates one radiation image based on the calculation result (by, for example, combining a plurality of image data whose entering positions and energy amounts are calculated).

In summary, the processor 120 detects each of radio-photons which have entered the pixel array APX when obtaining the image data DATA by analyzing each of the plurality of image data DATA. The processor 120 then calculates the entering position and energy amount of each of radio-photons based on a detection result on each radio-photon, and combines the calculation results with respect to the plurality of image data DATA, thereby generating one radiation image.

FIG. 7A is a flowchart for explaining an example of a method of detecting each radio-photon. Note that although each step in this flowchart can be mainly executed by the processor 120, some of the steps may be executed by other units as needed (the same applies to other flowcharts to be described later).

In subsequent steps S710 (to be simply referred to as "S710" hereinafter, and the same applies to other steps) to S760, the processor 120 sequentially scans pixel values constituting one image data DATA and specifies a portion, in the image data DATA, in which a pixel value has exceeded a predetermined value ("0" in this case) due to radio-photon detection. This operation is equivalent to specifying the detection area of a radio-photon in the pixel array APX upon obtaining the image data DATA.

In S710, the processor 120 selects a portion, of the image data DATA, which corresponds to the first pixel PX of the pixel array APX. Note that the respective pixels of the pixel array APX one-to-one correspond to the respective pixel values constituting the image data DATA, and the pixel array APX can be associated with the image data DATA. For the sake of easy explanation, the above operation is simply expressed as "the processor 120 selects a first pixel". For example, assuming that m and n are integers, and a pixel in the mth row and the nth column is expressed as a "pixel PX(m, n)", the pixel PX(1, 1) may be the first pixel.

In S720, the processor 120 determines whether the pixel PX selected in S710 satisfies conditions for a reference pixel PX_EV. Although described in detail later, the reference pixel PX_EV is a pixel as a reference for specifying the detection area of a radio-photon in the pixel array APX, and is a pixel serving as a starting point or start point of the specifying processing. The conditions for the reference pixel PX_EV include a condition that the pixel value of the pixel PX as a determination target should be larger than a predetermined threshold VTH1. That is, in this step, for example, the processor 120 determines whether the pixel value of the pixel PX is larger than threshold VTH1. If the pixel value of the pixel PX is larger than the threshold VTH1, the processor 120 selects the pixel PX as the reference pixel PX_EV. The process then advances to S730. In contrast to this, if the pixel value of the pixel PX is not larger than the threshold VTH1, the processor 120 does not select the pixel PX as the reference pixel PX_EV. The process then advances to S750.

The conditions for the reference pixel PX_EV may further include a condition that the pixel value of the pixel PX as a determination target should not be smaller than the pixel value of the adjacent pixel PX. This condition serves to set the pixel PX having a larger pixel value as the reference pixel PX_EV.

In addition, the conditions for the reference pixel PX_EV may include a condition that no flag should be set for the pixel PX as a determination target. Although described in detail later, a flag is a mark for indicating that the pixel PX is a target for predetermined processing. Setting a flag indicates that a condition for a target for the processing is satisfied. This condition serves to shorten the time required for processing in S720 to S760 by omitting processing for the pixel PX which has undergone the processing or omitting processing accompanying the processing.

In S730, the processor 120 refers to the pixel values of the pixels PX around the reference pixel PX_EV selected in S720 as a starting point, and specifies the detection area of a radio-photon in the pixel array APX. That is, in this step, the processor 120 specifies, as a detection area, an area which is a single area (a continuous area) in the pixel array APX and in which the pixel value of each pixel has become larger than 0 (reference value VTH2) upon entering of a radio-photon.

Note that S720 and S730 will be described in more detail later.

In S740, the processor 120 calculates the entering position and energy amount of a radio-photon based on the pixel value of each pixel in the detection area specified in S730, as described with reference to FIG. 5C.

In S750, the processor 120 determines whether the pixel PX selected in S710 is the last pixel. If the pixel PX is the last pixel, the processor 120 terminates this flowchart. Otherwise, the process advances to S760. Assume that X and Y are integers, and the pixel array APX has X rows and Y columns. In this case, when the pixel selected in S710 is a pixel PX(X, Y), the pixel PX(X, Y) is the last pixel, and the processor 120 terminates this flowchart. In contrast to this, if the pixel selected in S710 is a pixel PX(m, n) (m<X or n<Y), the process advances to S760.

In S760, the processor 120 can select the next pixel. If, for example, the pixel selected in S710 is the pixel PX(m, n) (n<Y), the processor 120 selects a pixel PX(m, n+1). If the pixel is a pixel PX(m, n) (m<X and n=Y), the processor 120 can select a pixel PX(m+1, 1).

FIG. 7B is a view for more specifically explaining the mode of the step (S720) of selecting a reference pixel. The processor 120 scans each pixel PX in each row as indicated by the arrows and the numerals in FIG. 7B, and sequentially determines whether each pixel PX satisfies a condition for the reference pixel PX_EV (that is, the pixel value of the pixel PX is larger than the threshold VTH1). More specifically, first of all, the processor 120 sequentially selects the respective pixels PX from the first column to the Yth column in the first row. Likewise, the processor 120 sequentially determines the respective pixels PX in the second and subsequent rows. FIG. 7B shows a case in which the pixel PX which satisfies the above condition exists in the fourth row (that is, a case in which the pixel PX having a pixel value larger than the threshold VTH1 exists in the fourth row). The detected pixel PX is selected as the reference pixel PX_EV. Assume that the pixel values of the four pixels PX adjacent to the reference pixel PX_EV in the row or column direction are not 0 but are not larger than the threshold VTH1, and hence these pixels are not selected as the reference pixel PX_EV.

FIG. 7C is a view for more specifically explaining the mode of the steps from the step of selecting the reference pixel PX_EV to the step of specifying a detection area (S720 and S730). To facilitate the visualization of the drawing, each portion whose pixel value is 0 is hatched, and each portion whose pixel value is larger than 0 exemplarily shows its numerical value. In addition, for the sake of easy explanation, FIG. 7C shows each row (R) and its number, and also shows each column (C) and its number.

For example, referring to an area P1 in FIG. 7C, when, for example, threshold VTH1=6, since the pixel value of a pixel PX(3, 3) in the third row and the third column is 10 (>VTH1), the pixel can be selected as the reference pixel PX_EV in S720. Note that the pixels PX around the pixel PX(3, 3) have pixel values smaller than VTH1 (=6), and hence these pixels are not selected as the reference pixel PX_EV.

Subsequently, in S730, the processor 120 can specify the area P1 as a detection area by referring to the pixel values of the pixels PX around the pixel PX(3, 3) selected as the reference pixel PX_EV as a starting point. In this case, for example, a result "38" obtained by adding the pixel values of the respective pixels PX in the area P1 can correspond to the energy amount of the radio-photon. In addition, in this case, for example, the pixel PX(3, 3) can correspond to the entering position of the radio-photon. In another case, the entering position of the radio-photon may be calculated from the weighted average of the pixel values of the respective pixels PX in the area P1 (that is, the barycentric position of the area P1 based on the pixel values may be set as the entering position of the radio-photon). In addition, the entering direction of the radio-photon may be collaterally calculated based on the pixel values of the respective pixels PX in the area P1. Alternatively, in this arrangement including the scintillator SC, the emission position of scintillation light may be calculated.

In addition, referring to an area P2 in FIG. 7C, when threshold VTH1=6 as in the above case, since the processor 120 determines in step S720 that the pixel values of all the nine pixels PX in the area P2 are smaller than VTH1, none of these pixels are selected as the reference pixel PX_EV.

The value of the threshold VTH1 may be set to a proper value for the selection of the reference pixel PX_EV. Properly setting the value of the threshold VTH1 can filter a portion, of the image data DATA, which is originated from noise, as indicated by the example of the area P2.

When an irregular radio-photon has entered, the pixel PX corresponding to the entering position of the radio-photon can have an excessively large pixel value. For this reason, in another case, a condition for the reference pixel PX_EV may be that the pixel value should be smaller than a predetermined value VTH0 (>VTH1) (the pixel value should fall within the range of VTH1 to VTH0). Cases in which an irregular radio-photon has entered include, for example, a case in which a photon of radiation (for example, cosmic radiation) different in type from radiation as a detection target has entered and a case in which a radio-photon has directly entered the detection element D (without being converted into light by the scintillator SC). This makes it possible to remove unintentional signal components from the image data DATA.

As described above, the conditions for the reference pixel PX_EV may further include a condition that the pixel value of the determination target pixel PX should not be smaller than the pixel values of the adjacent pixels PX. Assume that the pixel value of a given pixel PX is larger than VTH1. In this case, if the pixel value of the pixel PX is smaller than the pixel value of the adjacent pixel PX, the pixel PX may not be selected as the reference pixel PX_EV.

For example, referring to an area P3 in FIG. 7C, when threshold VTH1=6 as in the above case, the pixel value of a pixel PX(8, 3) in the eighth row and the third column is 8 (>VTH1) but is smaller than the pixel value "10" of an adjacent pixel PX(8, 4) in the eighth row and the fourth column. For this reason, in this case, in S720, the pixel PX(8, 3) is not selected as the reference pixel PX_EV. In this operation, in S720, the processor 120 may refer to the pixel value of the pixel PX adjacent to the pixel PX(8, 3) and compare the pixel value with that of the pixel PX(8, 3). In contrast to this, the adjacent pixel PX(8, 4) can be selected as the reference pixel PX_EV.

Subsequently, in S730, the processor 120 can specify the area P3 as a detection area by referring to the pixel values of the pixels PX around the pixel PX(8, 4) as the reference pixel PX_EV as a starting point. In this case, for example, a result "55" obtained by adding the pixel values of the respective pixels PX in the area P3 can correspond to the energy amount of the radio-photon. In addition, in this case, for example, the pixel PX(8, 4) can correspond to the entering position of the radio-photon. In another case, the entering position of the radio-photon may be calculated from the weighted average of the pixel values of the respective pixels PX in the area P3.

As described above, the detection area of a radio-photon in the pixel array AP is specified based on a result obtained by referring to the pixel values of the pixels PX around the reference pixel PX_EV as a starting point. More specifically, a detection area is specified by sequentially determining whether the pixel value of each pixel PX around the reference pixel PX_EV is larger than the reference value VTH2 (VTH2=0 in this case). This operation will be described below with reference to FIG. 8.

FIG. 8 is a flowchart for explaining "determination processing" forming part of an example of a detection area specifying method. The processor 120 performs the determination processing with respect to each pixel PX for which a flag is set. First of all, a flag is set for the reference pixel PX_EV selected in S720. A flag is a mark for indicating a determination processing target. Setting a flag for a given pixel indicates that the pixel has satisfied a condition for a determination processing target.

In S810, the processor 120 determines whether the pixel value of the pixel PX adjacent to a pixel for which a flag is set (the reference pixel PX_EV in this case) in the upper direction (one column direction) is larger than VTH2 (=0). If the pixel value of the adjacent pixel PX is larger than VTH2, the process advances to S811. Otherwise, the process advances to S820. In S811, the processor 120 determines whether the determination processing has already been performed with respect to the pixel value of the adjacent pixel PX. If the determination processing has been performed, the process advances to S820. Otherwise, the process advances to S812. In S812, a flat is set for the adjacent pixel PX. Subsequently, in S813, the processor 120 performs the same determination processing with respect to the new pixel PX for which the flag is set (the processor 120 performs processing in and after S810 with respect to the new pixel PX for which the flag is set).

In S820, the processor 120 determines whether the pixel value of the pixel PX adjacent to the pixel for which the flag is set in the rightward direction (one row direction) is larger than VTH2 as in S810. If the pixel value of the adjacent pixel PX is larger than VTH2, the processor 120 performs the same processing as that in S811 to S813. Otherwise, the process advances to S830. From S830, the processor 120 performs the same processing as that in S810 to S813 with respect to the pixel PX adjacent to the above pixel in the lower direction (the other column direction). From S840, the processor 120 performs the same processing as that in S810 to S813 with respect to the pixel PX adjacent to the above pixel in the leftward direction (the other row direction).

According to the above flowchart, the processor 120 performs the determination processing to determine whether each of the four adjacent pixels PX adjacent to the pixel PX for which the flag is set in the row or column direction is included in the detection area of the radio-photon in the pixel array APX. If there is any adjacent pixel PX determined to be included in the detection area, the processor 120 further performs the determination processing with respect to the adjacent pixel PX. Subsequently, the processor 120 repeats a similar procedure.

In other words, the processor 120 recursively performs the determination processing with respect to the pixels PX around the reference pixel PX_EV as a starting point. Alternatively, if the determination processing with respect to the reference pixel PX_EV is the first determination processing, it can be expressed that the Kth determination processing is performed with respect to each pixel PX determined to be included in a detection area by the (K−1)th determination processing (where K=2 to N). Note that N is an integer equal to or more than 2, and K is an integer equal to or more than 2 and equal to or less than N.

In this case, in the determination processing, the processor 120 determines whether each of the four pixels PX adjacent to the pixel PX for which a flag is set in the row or column direction (that is, adjacent in the opposite side directions of pixel partitions) is included in the detection area. However, determination targets are not limited to them. For example, each of the four pixels PX adjacent in the diagonal directions of pixel partitions may be the above determination target. Alternatively, each of a total of eight pixels PX adjacent in the opposite side direction or diagonal direction may be the above determination target.

In the above manner, detection areas of radio-photons are specified in the pixel array APX.

FIGS. 9A to 9H are views for explaining a specific example of using the detection area specifying method based on the flowchart exemplarily shown in FIG. 8. For the sake of easy understanding, VTH2=0, and each portion whose pixel value is 0 is hatched while each portion whose pixel value is larger than 0 (each portion to be specified as a detection area) is not hatched. In addition, for the sake of easy explanation, FIGS. 9A to 9H show each row (R) and its number, and also show each column (C) and its number. In this case, consider a case in which a pixel PX(4, 4) in the fourth row and the fourth column is selected as the reference pixel PX_EV.

In the step shown in FIG. 9A, the processor 120 performs the determination processing described with reference to FIG. 8 with respect to the reference pixel PX(4, 4). That is, in the area enclosed by the thick line, the pixel value of each of four adjacent pixels PX(3, 4), PX(4, 5), PX(5, 4), and PX(4, 3) adjacent to the reference pixel PX(4, 4) is a determination target for which it is determined whether it is larger than VTH2. In this case, since the pixel value of each of the four adjacent pixels PX(3, 4) and the like is larger than VTH2, a flag is set for each pixel.

In the step shown in FIG. 9B, the processor 120 performs determination processing with respect to the pixel PX(3, 4) of the four pixels for which flags are set in step in FIG. 9A. That is, the pixel values of the four adjacent pixels PX(2, 4), PX(3, 5), PX(4, 4), and PX(3, 3) adjacent to the pixel PX(3, 4) in the area enclosed by the thick line in FIG. 9B are targets to be determined whether being larger than VTH2. Since the pixel value of the adjacent pixel PX(3, 5) is larger than VTH2, a flag can be set. Since the pixel values of the adjacent pixels PX(2, 4) and PX(3, 3) are 0, no flag is set for the adjacent pixels PX(2, 4) and PX(3, 3). In addition, since determination processing has already been performed with respect to the adjacent pixel PX(4, 4), determination processing with respect to the adjacent pixel PX(4, 4) is omitted, and no flag is set.

In the step shown in FIG. 9C, the processor 120 performs determination processing with respect to the pixel PX(3, 5) for which a flag is set in the step in FIG. 9B according to the same procedure as that described above. Since the pixel value of the adjacent pixel PX(2, 5) is larger than VTH2, a flag can be set for the pixel. Since the pixel value of the adjacent pixel PX(3, 6) is 0, no flag can be set for the adjacent pixel PX(3, 6). In addition, since determination processing has already been performed with respect to the adjacent pixels PX(4, 5) and PX(3, 4), determination processing with respect to the adjacent pixels PX(4, 5) and PX(3, 4) is omitted, and no flag is set.

In the step shown in FIG. 9D, the processor 120 performs determination processing with respect to the pixel PX(2, 5) for which a flag is set in the step in FIG. 9C according to the same procedure as that described above. No flag is set for each of the four adjacent pixels PX adjacent to the pixel PX(2, 5).

Subsequently, in the step shown in FIG. 9E, the processor 120 performs determination processing with respect to the pixel PX(4, 5) of the four pixels for which flags are set in the step in FIG. 9A according to the same procedure. No flag is set for the four adjacent pixels PX adjacent to the pixel PX(4, 5).

In the step shown in FIG. 9F, therefore, the processor 120 performs determination processing with respect to the pixel PX(5, 4) of the four pixels for which flags are set in the step in FIG. 9A according to the same procedure. Since the pixel value of the adjacent pixel PX(5, 3) is larger than VTH2, a flag can be set for the pixel. No flag is set for the remaining adjacent pixels PX(4, 4), PX(5, 5), and PX(6, 4).

In the step shown in FIG. 9G, the processor 120 performs determination processing with respect to the pixel PX(5, 3) for which a flags is set in the step in FIG. 9F according to the same procedure. Since the pixel value of the adjacent pixel PX(6, 3) is larger than VTH2, a flag can be set for the pixel. No flag is set for the remaining adjacent pixels PX(4, 3), PX(5, 4), and PX(5, 2).

Repeating a similar procedure subsequently will specify the detection area of the radio-photon in the pixel array APX, as shown in FIG. 9H. Note that the sequence of setting flags is not limited to the above case, and may be changed within the spirit of the flowchart in this case and the spirit of the present invention.

According to this embodiment, for example, the pixel PX having a pixel value larger than threshold VTH1 is selected as the reference pixel PX_EV. Thereafter, the processor 120 sequentially refers to the pixel values of the respective pixels PX around the reference pixel PX_EV by performing determination processing with respect to the reference pixel PX_EV as a starting point. The processor 120 then specifies, as the detection area of the radio-photon in the pixel array APX, an area including the pixels PX whose pixel values are larger than the reference value VTH2 (<VTH1) and the reference pixel PX_EV. It is possible to calculate the entering position and energy amount of a radio-photon in the pixel array APX based on the pixel values of the respective pixels in the specified detection area. The processor 120 can perform these processes with respect to each of the plurality of image data while sequentially receiving a plurality of image data or upon receiving all the plurality of image data.

The threshold VTH1 may be set to a proper value for the selection of the reference pixel PX_EV. Properly setting the value of the threshold VTH1 can filter a portion, of the image data DATA, which is originated from noise. In addition, this makes it possible to discriminate a portion originated from an irregular radio-photon.

This embodiment has exemplified the mode of selecting the reference pixel PX_EV by comparing the threshold VTH1 with a pixel value. However, the method of selecting the reference pixel PX_EV is not limited to this method as long as the reference pixel PX_EV can be selected. In addition, as described above, conditions for selecting the pixel PX as the reference pixel PX_EV may collaterally include a condition that the pixel value of the pixel PX should not be smaller than the pixel values of the adjacent pixels PX or that no flag should be set for the pixel PX.

In addition, this embodiment has exemplified the case in which the reference value VTH2 is "0". However, the reference value VTH2 need not be "0" as long as it is smaller than the threshold VTH1 ("6" in this embodiment). When, for example, specifying the detection area of a radio-photon in the pixel array APX while filtering noise components such as system noise, it is possible to set the reference value VTH2 to a value larger than $4\sigma$ where $\sigma$ is the standard deviation of the noise components.

Furthermore, this embodiment has exemplified the case in which if the pixel value of the pixel PX is larger than the reference value VTH2, it is determined that the pixel PX is included in the detection area of the radio-photon. However, the present invention is not limited to this. If, for example, the pixel value of a given pixel PX indicates that a radio-photon has entered the pixel array APX, the pixel PX may be configured to be included in the detection area. That is, the above determination need not be performed by comparison between a pixel value and a fixed value. For example, it may be determined whether a pixel PX adjacent to a reference target pixel PX (one pixel to which attention is paid to specify a detection area) is included in the detection area, based on the relationship (a result of comparison between) the pixel value of the reference target pixel PX and the pixel value of the adjacent pixel PX. If, for example, the pixel value of the adjacent pixel PX is smaller than the pixel value of the reference target pixel PX, the adjacent pixel PX may be included in the detection area. That is, based on the pixel value of a reference target pixel and the pixel values of neighboring pixels (based on whether they are originated from entering of a radio-photon into the pixel array APX), it may be determined whether they or some of them satisfy the conditions for the detection area.

As described above, this embodiment is advantageous in specifying the detection area of a radio-photon in the pixel array APX and accurately calculating the entering position and energy amount of the radio-photon.

Second Embodiment

As described above, the processor 120 calculates the entering positions and energy amounts of radio-photons in the pixel array APX with respect to the plurality of image data DATA, and generates one radiation image based on the calculation results (by, for example, combining a plurality of image data). The first embodiment described above is configured to perform the above calculation by referring to the pixel value of the reference pixel PX_EV and the pixel values of the neighboring pixels PX in one image data DATA. The second embodiment differs from the first embodiment in that it further uses other image data DATA before and/or after the above image data DATA.

Like FIG. 8, FIG. 10 shows a flowchart for explaining "determination processing" forming part of an example of a detection area specifying method according to this embodiment. Consider, for example, a case in which a pixel for which a flag is set (a reference pixel PX_EV selected in S720 described above in this case) corresponds to image data DATA(t) obtained at time t.

In this case, in S1010, it is determined whether the pixel value of a corresponding pixel PX is larger than VTH2 (=0) in image data DATA(t−Δt) obtained at the immediately preceding timing (for example, the timing earlier than time t by Δt). If the pixel value of the pixel PX is larger than VTH2, the process advances to S1011. Otherwise, the process advances to S1020. Since the contents of processing in S1011 to S1013 are the same as those in S811 to S813 described above, a description of them will be omitted.

In and after S1020, the same processing as that in S1010 to S1013 is performed with respect to the corresponding pixel PX of image data DATA (t+Δt) obtained at the immediately succeeding timing (for example, the timing later than time t by Δt). Subsequently, the same processing as that shown in FIG. 8 can be performed (the process advances to S810).

FIG. 11 is a view for explaining a specific example of a detection area specifying method based on the above flowchart. Referring to FIG. 11, the X-axis corresponds to the row direction, and the Y-axis corresponds to the column direction. In addition, the t-axis represents the time axis. According to the above flowchart, first of all, a reference pixel PX_EV(t) is selected in the image data DATA(t) at time t. It is possible to refer to the pixel values of a reference pixel PX_EV(t−Δt) and neighboring pixels with respect to the image data DATA(t−Δt) at time t−Δt. In addition, it is possible to refer to the pixel values of a reference pixel PX_EV(t+Δt) and neighboring pixels with respect to the image data DATA(t+Δt) at time t+Δt. Thereafter, it is possible to refer to the pixel values of a reference pixel PX_EV(t) and neighboring pixels with respect to the image data DATA(t) at time t. The same applies to another reference pixel PX_EV2(*t*). Note that the above sequence of referring to pixel values is not limited to this, and may be changed within the spirit of this case and the spirit of the present invention.

According to this embodiment, using pixel values at the entering timing of a radio-photon and preceding and succeeding timings make it possible to calculate the entering position and energy amount of the radio-photon with higher accuracy than in the first embodiment.

Although this embodiment has exemplified the mode of using the image data DATA(t−Δt) and DATA(t+Δt) in addition to the image data DATA(t), it is possible to further use image data DATA at a further preceding timing and/or a further succeeding timing. In addition, using a plurality of image data DATA at different timings makes it possible to further calculate the attenuation amount or rate of scintillation light. This can further improve the accuracy of calculation.

(Others)

Although some preferred embodiments have been exemplarily described above, the present invention is not obviously limited to them. Part of each embodiment may be modified without departing from the spirit and scope of the invention. In addition, each embodiment described above has referred to the so-called "indirect conversion type" arrangement which converts radiation into light by using the scintillator SC and converts the light into an electrical signal by using the detection element D. However, the present invention may be applied to a so-called "direct conversion type" arrangement which directly converts radiation into an electrical signal.

In addition, each term described in this specification is merely used for the purpose of explaining the present invention. Obviously, the present invention is not limited to the strict meaning of each term, and can include equivalents of the respective terms.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-223341, filed Nov. 13, 2015, which is hereby incorporated by reference herein in its entirety.

The invention claimed is:

1. A radiation imaging apparatus, comprising:
a pixel array in which a plurality of pixels are arrayed; and
a processor configured to generate a radiation image based on radio-photons which have entered the pixel array, wherein the processor performs
a first process of obtaining a value of a signal from each of the plurality of pixels as a pixel value,
a second process of selecting at least one of the plurality of pixels as a reference pixel, and
a third process of specifying a detection area of a radio-photon in the pixel array by sequentially referring to pixel values of pixels around the reference pixel as a starting point.

2. The apparatus according to claim 1, wherein in the third process, the processor determines whether the referred pixel value is originated from entering of a radio-photon into the pixel array, and specifies an area including the pixel of the pixel value and the reference pixel as the detection area when the pixel value is originated from entering of a radio-photon into the pixel array.

3. The apparatus according to claim 1, wherein in the third process, the processor specifies an area including the pixel whose referred pixel value is larger than a reference value and the reference pixel as the detection area.

4. The apparatus according to claim 3, wherein in the second process, the processor selects a pixel whose pixel value is larger than a threshold larger than the reference value as the reference pixel.

5. The apparatus according to claim 3, wherein the plurality of pixels are arrayed in a matrix pattern in the pixel array,
the processor has a function of determining whether each pixel adjacent to a given pixel in a row direction or a column direction is included in the detection area, based on whether a pixel value of each adjacent pixel is larger than the reference value, and
in the third process the processor performs, a first determination process of performing the determination with respect to the reference pixel, and a Kth determination process of performing the determination with respect to each of the adjacent pixel determined to be included in the detection area by a (K−1)th determination process, where N is an integer not less than 2 and K is an integer not less than 2 and not more than N with respect to K from 2 to N.

6. The apparatus according to claim 1, wherein the plurality of pixels include a first pixel and a second pixel which are adjacent to each other, and
the processor does not select the first pixel as the reference pixel in the second process when a pixel value of the first pixel is smaller than a pixel value of the second pixel.

7. The apparatus according to claim 1, wherein the processor removes a pixel value, of pixel values obtained in the first process, which is originated from radiation of a type other than a detection target, based on a pixel value of each pixel in the detection area.

8. The apparatus according to claim 1, wherein the processor performs a fourth process of calculating an entering position of a radio-photon in the pixel array and an energy amount of the radio-photon based on a pixel value of each pixel in the detection area.

9. The apparatus according to claim 8, wherein the processor further calculates an entering direction of the radio-photon based on a pixel value of each pixel in the detection area in the fourth process.

10. The apparatus according to claim 8, further comprising a scintillator, wherein in the fourth process the processor further calculates an emission position of the scintillator based on a pixel value of each pixel in the detection area.

11. The apparatus according to claim 8, wherein the processor obtains a plurality of image data in the first process by performing in a predetermined cycle a series of operations of obtaining one image data by reading out a signal from each of the plurality of pixels, and
in the fourth process the processor calculates an entering position of the radio-photon and an energy amount of the radio-photon by using the plurality of image data.

12. The apparatus according to claim 11, wherein the processor performs the second process and the third process with respect to first image data of the plurality of image data, and
performs the second process and the third process with respect to second image data as another image data obtained at a timing preceding and/or succeeding a timing at which the first image data is obtained, when the detection area is specified with respect to the first image data by the second process and the third process.

13. The apparatus according to claim 12, wherein a pixel position of the reference pixel selected by the second process with respect to the first image data corresponds to a pixel position of the reference pixel selected by the second process with respect to the second image data.

14. A photon counting method using the radiation imaging apparatus according to claim 1 having said pixel array in which a plurality of pixels are arrayed and which is used to detect a radio-photon, the method comprising the steps of:
obtaining a pixel value by quantizing a signal from each of the plurality of pixels;
selecting at least one pixel of the plurality of pixels as a reference pixel; and
specifying a detection area of a radio-photon in the pixel array by sequentially referring to pixel values of pixels around the reference pixel as a starting point.

15. A radiation imaging apparatus, comprising:
a pixel array in which a plurality of pixels are arrayed; and
a processor configured to generate a radiation image based on radio-photons which have entered the pixel array, wherein the processor performs
a first process of obtaining a value of a signal from each of the plurality of pixels as a pixel value,
a second process of selecting at least one of the plurality of pixels as a reference pixel, and
a third process of specifying a detection area of a radio-photon in the pixel array based on a pixel value of the reference pixel and pixel values of pixels around the reference pixel.

16. The apparatus according to claim 15, wherein the plurality of pixels are arrayed in a matrix pattern in the pixel array,
the processor has a function of determining whether each pixel adjacent to a given pixel in a row direction or a column direction is included in the detection area, based on whether a pixel value of each adjacent pixel is larger than the reference value, and
in the third process the processor performs a first determination process of performing the determination with respect to the reference pixel, and a Kth determination process of performing the determination with respect to each of the adjacent pixel determined to be included in the detection area by a (K - 1)th determination process, where N is an integer not less than 2 and K is an integer not less than 2 and not more than N with respect to K from 2 to N.

17. The apparatus according to claim 15, further comprising a scintillator, and wherein the processor further performs a fourth process of:
- calculating an entering position of a radio-photon in the pixel array and an energy amount of the radio-photon based on a pixel value of each pixel in the detection area, and
- calculating an emission position of the scintillator based on a pixel value of each pixel in the detection area.

18. A photon counting method using a pixel array in which a plurality of pixels are arrayed and which is used to detect a radio-photon, the method comprising the steps of:
- obtaining a pixel value by quantizing a signal from each of the plurality of pixels;
- selecting at least one pixel of the plurality of pixels as a reference pixel; and
- specifying a detection area of a radio-photon in the pixel array based on a pixel value of the reference pixel and pixel values of pixels around the reference pixel.

* * * * *